(12) United States Patent
Forber

(10) Patent No.: US 6,932,831 B2
(45) Date of Patent: Aug. 23, 2005

(54) VASCULAR PROTECTION SYSTEM

(75) Inventor: Simon John Forber, Puy Lonchard (FR)

(73) Assignee: B. Braun Medical SAS, Boulogne-Billancourt (FR)

( * ) Notice: Subject to any disclaimer, the term of this patent is extended or adjusted under 35 U.S.C. 154(b) by 462 days.

(21) Appl. No.: 10/193,678

(22) Filed: Jul. 12, 2002

(65) Prior Publication Data

US 2003/0023265 A1 Jan. 30, 2003

(30) Foreign Application Priority Data

Jul. 13, 2001 (FR) .............................................. 01 09427
Oct. 25, 2001 (FR) .............................................. 01 13815

(51) Int. Cl.[7] ........................ A61B 17/22; A61M 29/00
(52) U.S. Cl. .................................................. 606/200
(58) Field of Search ................................ 606/200, 159

(56) References Cited

U.S. PATENT DOCUMENTS 6,336,934 B1 * 1/2002 Gilson et al. ............... 606/200
6,468,291 B2 * 10/2002 Bates et al. ................. 606/200
6,702,834 B1 * 3/2004 Boylan et al. .............. 606/200
2001/0031981 A1 * 10/2001 Evans et al. ................ 606/200

FOREIGN PATENT DOCUMENTS

| WO | WO 99/23976 A1 | 5/1999 |
| WO | WO 99/44542 A2 A3 | 9/1999 |
| WO | WO 00/67665 A1 | 11/2000 |

* cited by examiner

Primary Examiner—Anhtuan T. Nguyen
Assistant Examiner—Elizabeth Houston
(74) Attorney, Agent, or Firm—Rothwell, Figg, Ernst & Manbeck (57) ABSTRACT

Vascular protection system comprising a radially expandable filtering element (10) permeable to blood but impermeable to embolic materials, comprising a membrane (9') linked to a hollow support structure made up of a succession of wires ($70'_1$, $70'_2$). The support structure comprises at least two groups (34, 36) of wires, each having more than two mutually adjacent wires, these groups being parted at a point on the length of the wires so that at least some of the wires within one of the groups part from one another, after which, farther along this length, the wires of a specific group which part from at least some of the other wires of this same group rejoin at least one wire of (one of) the other group(s) of wires.

11 Claims, 7 Drawing Sheets

FIG_6

FIG_7

FIG_10

FIG_11

FIG.12

FIG_13

FIG_14

FIG_15

VASCULAR PROTECTION SYSTEM

The invention relates to a vascular protection or treatment system which can be implanted through an endoluminal access in a blood vessel wall. More specifically, it is designed to trap embolic materials constituting "vascular debris" or bodies transported by the blood and which must be prevented from migrating to dangerous zones. It is also designed to prevent the risk of inopportune vascular occlusion.

Accordingly, the objective of the invention is to propose a system that will enable this vascular debris to be collected, in particular during an angioplasty treatment.

The system proposed by the invention may also be applied for the purpose of implanting a stent for an atherectomy or a thrombectomy in a blood vessel.

Given that the problem of vascular debris (also referred to as embolic materials) inside a vessel poses major risks to the patient, vascular protection systems have already been proposed, for example in patent specifications WO-A-99/44542 or WO-A-99/23976.

However, one problem which persists is that of achieving penetration in a manner which promotes the flow of blood into the filtering element in conjunction with the problem of providing a seal by this filtering element (more specifically, its membrane in the region of the edge of its proximal opening) and the internal wall of the vessel against which the membrane must be applied (locally), when the filtering element is in the radially deployed state.

In patent specification WO-A-99/23976, the inverted cone arrangement of the wires forming the support structure, on the one hand, and the filtering membrane, on the other, are conducive to providing a relative seal.

Patent specification WO-A-99/44542 describes the presence of a mouth of metal wire, which extends around the perimeter in the region of the proximal edge of the filtering edge.

Nevertheless, a sufficiently effective compromise has not been found between the need to provide a perfect seal between filtering element and internal vessel wall, to provide the best possible opening of the filtering member in the region of its proximal edge (blood to be channelled so that it can be filtered in situ), a very reliable radial opening/folding action which needs to be obtained for the filtering element and/or a compact arrangement.

In this respect, the support structure must assist the membrane during radial opening and closing and prevent it from becoming trapped or causing a delayed reaction, whilst ensuring the best possible peripheral seal with the internal wall of the vessel.

One solution to this problem proposed by the invention, not disclosed in the above-mentioned prior art, is that the support structure locally defines a peripheral mouth at its external perimeter, this mouth being substantially continuous and co-operating with the proximal edge of the membrane so as to support it at this point.

To improve control of radial opening/closing operations (expansion/retraction) of the filtering membrane still further whilst promoting the flow of blood into the pocket formed by this membrane, the invention additionally recommends that:
the wires of the support structure have a proximal end and a distal end, where they are mutually joined respectively by proximal and distal rings, and
the proximal and distal portions of several successive wires are substantially parallel and adjacent around the axis, with one wire is at an angular offset between the adjacently disposed wires along their proximal portion and their distal portion.

Moreover, to improve the seal between the filtering element and the internal wall of the vessel as well as the general filtration efficiency of the system whilst maintaining a good flow of blood during this in situ filtering operation, another feature proposed by the invention is that when the filtering element is in a radially expanded position, the proximal portions of the wires together define a cone shape and the distal portions of these same wires together substantially define a cylinder adjoining a distal cone, where the filtering membrane is permeable to blood, the cylinder of the distal portions also being joined to the cone of the proximal sections, substantially at the proximal edge of the membrane, by the intermediate portions of the wires.

In a complementing manner, the membrane is sealed to prevent ingress of blood in the region of the cylinder defined by the distal portions of the wires, said membrane having openings to allow a passage for the blood but not vascular debris, in the region of the distal cone defined by said distal portions of the wires.

To assist manufacture of the support structure whilst making use of the mechanical effects required of the membrane, the invention proposes another feature whereby the intermediate portion of one of the wires forming the structure is joined at one end to the proximal portion and at another end to the distal portion of the same wire by rounded elbows subtending an angle $\alpha$ such that $90°<\alpha<135°$.

To obtain a high-performance protection system which meets the above-mentioned requirements with regard to opening/closing quality, seal and manufacture, another key aspect of the invention is a design whereby:
from the proximal edge of the filtering element to its distal end, the membrane advantageously covers, and is therefore supported by, the support structure, which, in conjunction with the membrane, has a locally cylindrical shape when the filtering element is in the radially expanded state, thus defining a cylindrical sealing surface with a vascular wall where the protection system is to be implanted,
and, by preference, the cylindrical sealing surface is of an axial length longer than (preferably at least twice as long as) the axial length of the proximal and distal cones defined by the wires at the respective proximal and distal ends of the filtering element,
and/or the intermediate portions of the wires together substantially define in pairs, around the perimeter, a series of adjacent arches at their ends.

Another solution proposed by the invention as a means of ensuring that the membrane is efficiently secured and is conducive to the radial deployment of the support structure is that the support structure of the protection system described above has, from the proximal end to the distal end, firstly at least two groups of wires, each with more than two mutually adjacent wires, these groups parting at a point along the length of the wires so that, within the groups, at least some of the wires diverge from one another, then, farther along this length, some wires of a specific group which diverge from at least some of the other wires of this same group join back up again in an arrangement adjacent to at least one wire of (one of) the other group(s) of wires.

Reducing the limit of the groups of wires, on the proximal side, to two groups in this manner also enables two large inlet orifices to be obtained, as will be explained below.

Still on the proximal side, the fact of providing each of these two groups with more than two mutually adjacent wires also increases the reliability with which the filtering element opens, particularly in the zone of the inlet orifices.

It should also be pointed out that the gap between the wires of a given group, followed, farther on along the length, by a converging arrangement with at least some of the wires of another group, assists radial deployment, the function of maintaining the membrane against the vessel wall in the operating position and the transverse supporting zones of this membrane (typically where the wires diverge from the group constituting the proximal side at the outset).

In relation to the above, a complementary objective of the invention is to ensure that the membrane is maintained particularly securely against the internal wall of the vessel, on the second and third parts of the length of the wires (i.e. from the point at which at least some of the wires of the proximal group diverge from the other wires in the group).

Apart from this mechanical effect, it is also desirable to secure an improvement in radio opacity.

To this end, one complementary feature proposed by the invention is that, at the point where the groups of wires part, at least some of the wires of each group diverge from the other wires of the same group, whilst other wires of this group remain joined in an adjacent fashion and remain so, across at least a part of the rest of their length (it being pointed out that, along the part of the length of the wires closer to the distal end, the radial holding action may be regarded as less sensitive given that the membrane is typically spaced apart from the vessel there, where it has a substantially conical portion adjoining the distal end of the filtering element).

As a means of achieving at least some of the objectives listed above and in the best manner possible, the invention advantageously proposes another feature whereby, close to the proximal end, the support structure exclusively comprises two groups of at least four wires each, parting at a point along the length of the wires such that, a first wire in each group is spaced apart to one side, a second wire to the other and the third and fourth wires of the same group remain together, whereas farther on along the length, said first wire rejoins a first wire of the other (another) group and said second wire rejoins a second wire of this other group.

The invention is also intended to provide an efficient solution to the problem of retaining the wires of the support structure when they have to be adjacent to one another, an additional secondary objective being to increase the radio-opacity of the filtering element to as high a degree as possible.

To this end, the invention proposes another feature whereby, at least at a point at which the wires of the support structure are disposed in an adjacent arrangement, these wires are locally enclosed in a ring having a peripheral wall, through which the wires are joined to one another by weld spots.

A more detailed description of the invention will now be given with reference to the appended drawings, of which.

Figure 1:
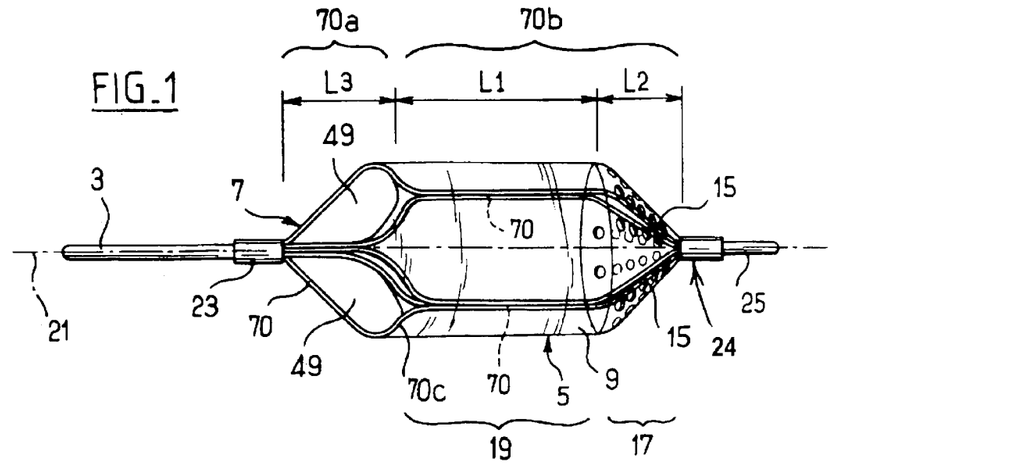
FIG. 1 is a view showing a slight perspective of a distal portion of a vascular protection system as proposed by the invention, specifically showing the filtering element.
Figure 2:
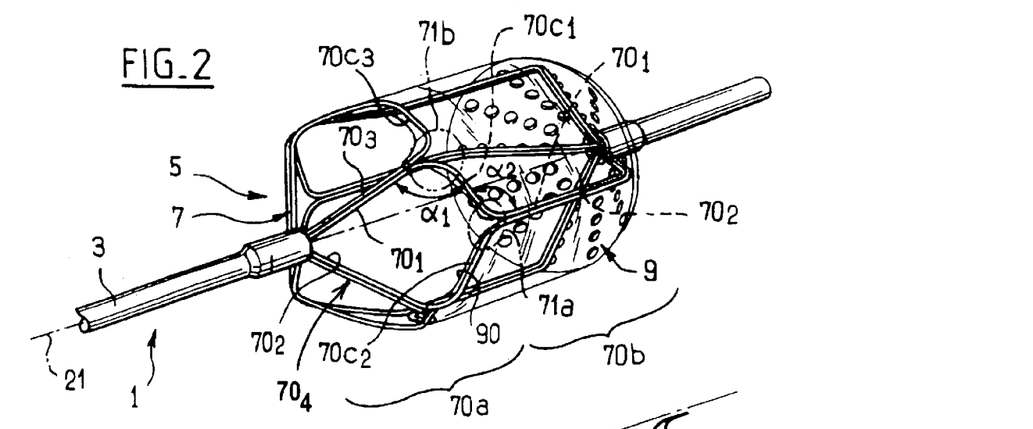
FIG. 2 shows the same portion as FIG. 1, from a proximal perspective.
Figure 6:
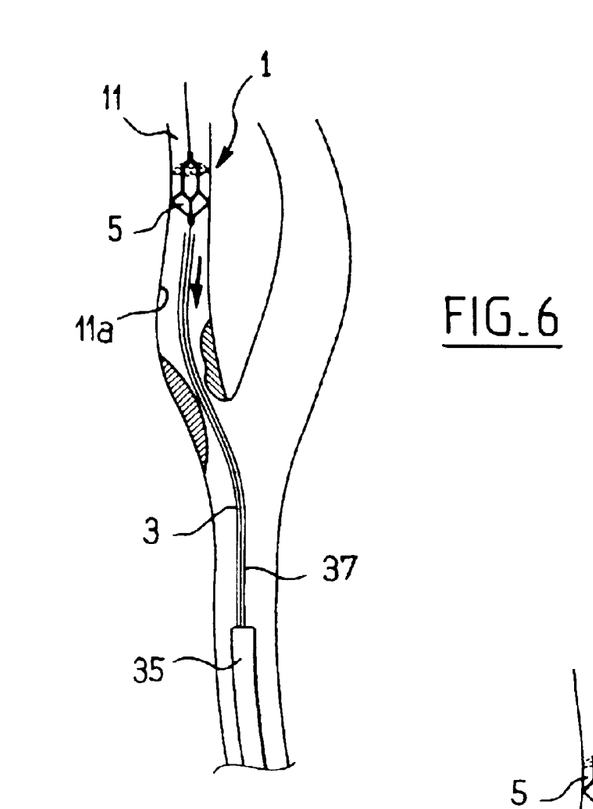

FIGS. 1, 2 and 6 will be described first of all to provide an explanation of a vascular protection system 1 as proposed by the invention.

The vascular protection system 1 has a wire guide 3 fixed to a distal filtering element 5, which in turn essentially comprises an automatically and radially expandable support structure 7 and a filtering membrane 9 defining a radially deformable pocket.

The wire guide 3 is either a flexible wire, such as a metal wire, or a fine catheter. It is long enough to reach the vascular region to be protected (such as the internal carotid region 11 of FIG. 6, for example), from outside the patient's body, i.e. from the outer cutaneous surface denoted by reference 13 in FIG. 4.

Given the flow of body fluid which must pass through it, the membrane 9 is preferably made from an impermeable polymer plastics film, locally perforated with distal orifices 15 to allow a passage for the body fluid. However, it would also be conceivable to use a porous material, such as polyurethane for example. Mesh might also be suitable. However, it is recommended that the filter 9 be porous to the body fluid (blood in particular) exclusively at its substantially conical distal portion 17, whereas the filter will be substantially impermeable at the cylindrical proximal portion 19 which has an essentially constant and substantially circular section.

The filter sheet (or membrane) 9 is joined to the support structure 7 for the purpose of its deployment and radial folding, i.e. substantially perpendicular to the general axis 21 of the vascular protection system (which axis coincides with the axis of the wire guide 3).

On its periphery, the support structure 7 has a succession of wires 70 which extend globally parallel with the axis 21 and which have a proximal portion 70a and a distal portion 70b joined to one another by an intermediate portion 70c, disposed transversely to the axis 21.

As may be seen more clearly from FIG. 2, (on the perimeter of the filtering element) the transverse intermediate portions such as $70c_1$, and $70c_2$ of two successive wires such as $70_1$ and $70_2$, have a mutually adjacent end defined by the zone 71a.

In the preferred example illustrated, the proximal and distal portions 70a and 70b of several successive wires are even substantially adjacent across their entire length, with one wire offset at an angle about the axis 21, between the wires that are disposed in an adjacent arrangement, along their proximal portion and their distal portion.

Accordingly, at their proximal portion 70a, wires $70_1$, and $70_3$ are parallel and adjacent, edge to edge, after which wire $70_1$ becomes parallel and adjacent, again edge to edge, with wire $70_2$ at the distal portion 70b. Between the two portions, the intermediate portion $70c_1$ of wire $70_1$ is adjacent, towards the end zone 71b, to the intermediate portion $70c_3$ of the filter $70_3$, whilst it is adjacent to the intermediate portion $70c_2$ of the filter $70_2$ at its other end, in the region of the adjoining zone 71a.

This configuration, repeated around the periphery of the filtering element 5, is such that the succession of intermediate portions of the wires ($70c_1$, $70c_3$ and so on) defines a substantially continuous perimeter mouth, which will assist in positioning the membrane 9, the proximal edge 90 of which (proximal end) will conform to the contour of this open mouth and be supported against it.

To open the filtering element radially, the proximal portion 70a of the structural wires is substantially conical, whereas each distal portion 70b of the wires is initially cylindrical in section (along the axial length $L_1$ of portion 19 of the membrane 9), and then substantially conical along the axial length $L_2$ corresponding to portion 17 of the membrane.

The proximal edge 90 of the membrane and the open mouth defined by the succession of transverse, intermediate portions of wires are located substantially at the point where the conical and cylindrical portions of the wires 70a, 70b meet.

Figure 3:
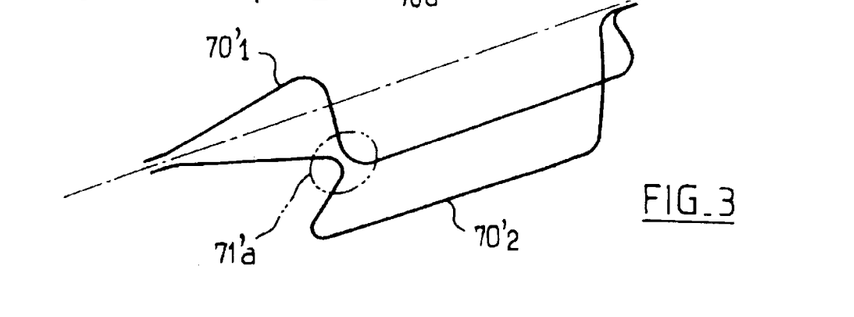
FIG. 3 is a diagram showing another arrangement of two of the structural wires of the filtering element.

The fact that the proximal and distal ends of the filtering elements are shaped in the form of two inverted cones will enable the wires, or supports, 70, to be clamped, on the proximal side, in a first ring 23 which provides the link between the filtering element 5 and the wire guide 3 and, on the distal side, in a second ring 24 joined to a flexible end-piece ("floppy end") 25. It should be pointed out that such an arrangement of wires with portions of wires doubling up (except for the region of the intermediate connecting portions $70c_1$, $70c_3$, . . . ) is preferred, rather than an arrangement of wires all in the same direction on the periphery of the opening mouth, as illustrated in FIG. 3, where no portions are doubled up (except at their proximal and distal ends, the wires such as $70'_1$, $70'_2$ are not adjacent in their radially deployed state except at a single end of their intermediate portion, at 71'a). The preferred solution of FIGS. 1 and 2 assists radial maneuvering of the filtering element and improves the seal with the internal wall of the vessel.

With regard to this seal, it should be pointed out that if portion 19 has a substantially constant section along its length $L_1$, the sealing properties will be better than the currently known conical or frustoconical shaping from the proximal opening end of the membrane to the distal end of the filtering element (as disclosed in patent specification WO-A-99/23976 or WO-A-99/44542).

By preference, the length $L_1$ will be between 2 and 4 times the lengths $L_2$ and $L_3$ ($L_3$ being the axial length of the proximal portion 70a), $L_2$ and $L_3$ being such that $L_2 \leq L_3 \leq 1,5L_2$, with a view to optimizing sealing properties and the conditions for opening/closing the filtering element 5.

The wires 70 may be metal (in particular stainless steel) or have a thermal type memory ("Nitinoi"®, in particular), or even be of a synthetic material. On the proximal side, the arrangement comprises at least two groups of wires (in this instance, four) each having two wires such as $70_1$, $70_3$, in one group, or alternatively, $70_2$, $70_4$, for another group, these wires being adjacent to one another along the length $L_3$ (in this instance, edge to edge and rectilinear). At the end of this length $L_3$, which starts at the point of the proximal ring 23 and extends substantially as far as the boundary of the opening mouth 90 of the membrane, the groups part.

Accordingly, wires $70_1$, $70_3'$ for example, diverge from one another in the region of zone 71b following a curvature such that, shortly after their lengthwise run, these parted wires meet up again adjacent to a wire of another group. In this example, it may be noted that wire $70_1$ converges with $70_2$ and wires $70_4$ and $70_3$ in turn individually converge with a wire of another group, not shown by reference.

As may also be noted, this convergence is effected along the length $L_1$, the wires (such as $70_1$, and $70_2$) on this length being parallel with the axis 11, whereas, although remaining essentially straight, they assume a conical ring both along the proximal length $L_3$ and on the distal length $L_2$ in the region at which the rounded base of the membrane 9 is located.

To ensure that the support structure 7 is reliable and is conducive to obtaining the advantages listed above, it may also be noted that the intermediate portions of wires $70c_1$ . . . connect with the proximal and distal portions of the same wires (such as $70_1$) by rounded elbows subtending an angle (respectively $\alpha_1$ in the case of the proximal join and $\alpha_2$ in the case of the distal join, in FIG. 2) so that each angle ($\alpha_1$, $\alpha_2$) is between approximately 90° and 135°.

The peripheral opening mouth of the membrane 9, and the intermediate portions of wires $70c_1$, $70c_2$, . . . define in pairs a succession of adjacent arches. Advantageously, the filter structure 9 will be disposed externally to the support structure 7, supported against the distal portion 70b.

The membrane may be bonded to the structure wires.

Turning to FIGS. 4 to 11, an explanation will now be given of the operating procedure for using the temporary vascular protection system described above.

Figure 4:
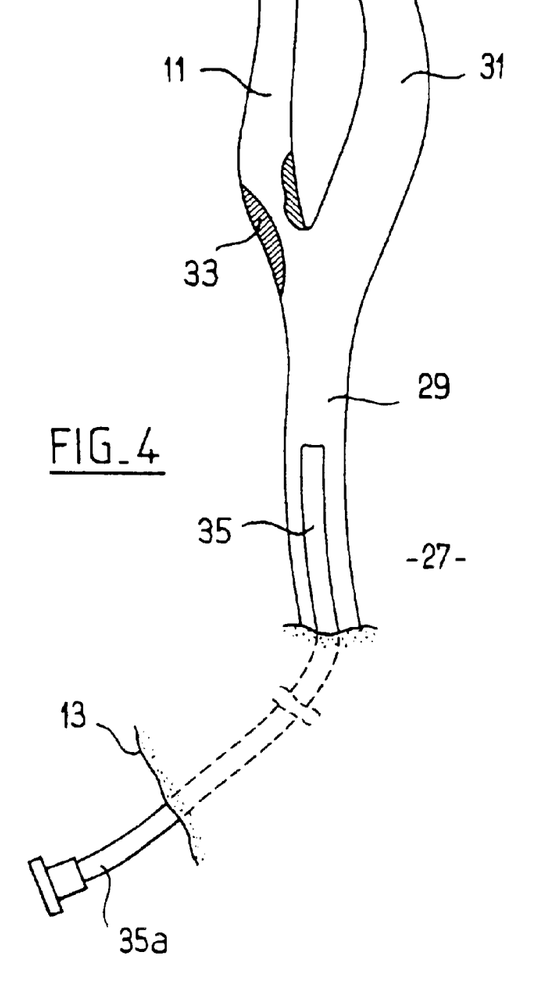
FIGS. 4, 5, 6, 7, 8, 9, 10 and 11 are diagrams on a smaller scale illustrating the main operating steps for implanting and then removing a vascular protection system as proposed by the invention.

FIG. 4 specifically shows a cutaneous surface 13 of a body 27, as well as a carotid 29 which splits into an outer carotid 31 and an inner carotid 11. At the point where the inner carotid 11 branches off is a stenosis 33. The vascular protection device 1 will be used to treat this stenosis whilst protecting the heart against embolisms.

To this end, the practitioner firstly introduces a catheter guide 35 through the skin 13 and as far as the carotid 29, the proximal end 35a of which is left sticking out from the patient's body.

Figure 5:
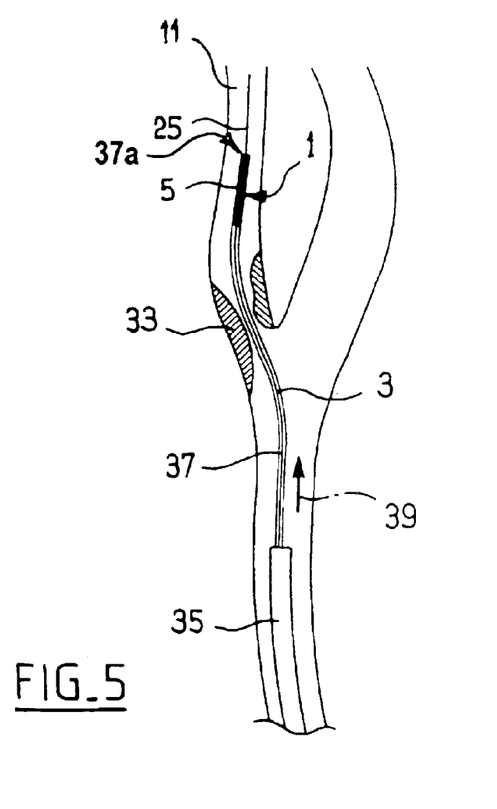

As may be seen from FIG. 5, an insertion catheter 37 has been slid through the catheter guide 35 (and has been so from outside the patient's body). Placed in the insertion catheter 37 (the diameter of which will typically be 4F), is the vascular protection device 1 proposed by the invention comprising the filtering element 5 maneuverable by its wire guide 3 (the proximal end of which, not illustrated, naturally emerges from the patient's body so as to be maneuverable from outside this body).

The distal end-piece 25 acts as a flexible guide and extends out beyond the distal end 37a of the catheter 37.

In this state, the filtering element 5 is retracted, radially constrained by the catheter 37, which encloses and radially compresses it.

At the outlet of the catheter guide 35, the practitioner moves the catheter 37 past the stenosis 33, bringing its distal end 37a downstream, in the inner carotid 11. The direction of blood flow is indicated by arrow 39.

In FIG. 6, the insertion catheter 37 has been pulled back towards the rear, whereas the filtering element 5, which is automatically radially expandable, is held in place, so that it is removed from the catheter and is radially open in a position such as that illustrated in FIGS. 1 and 2.

The filtering element or temporary filter 5 is therefore placed against the internal wall 11a of the carotid 11 with which a seal is now formed.

Figure 7:
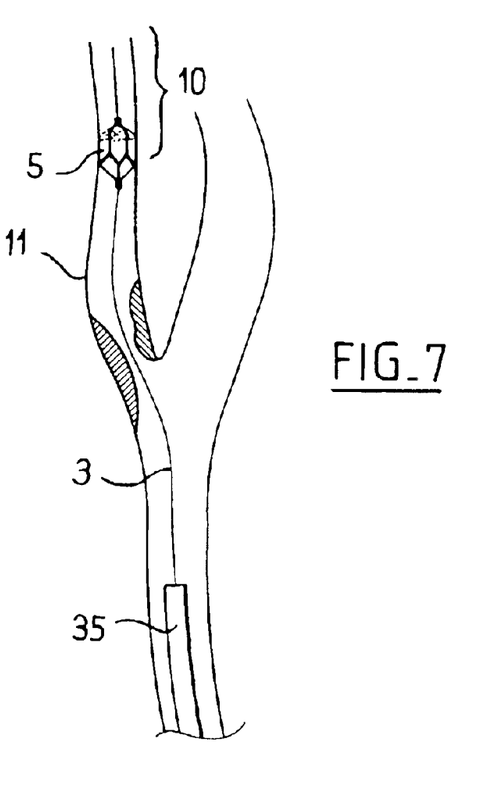

The insertion catheter 37 is then withdrawn through the catheter guide 35 (see FIG. 7). The filter 5 protects the vascular region 10 and all the rest of the vessel beyond.

To reduce the stenosis 33, the practitioner can then introduce a catheter 39 with a small deflated balloon 41 via the same access comprising the catheter guide 35.

Figure 8:
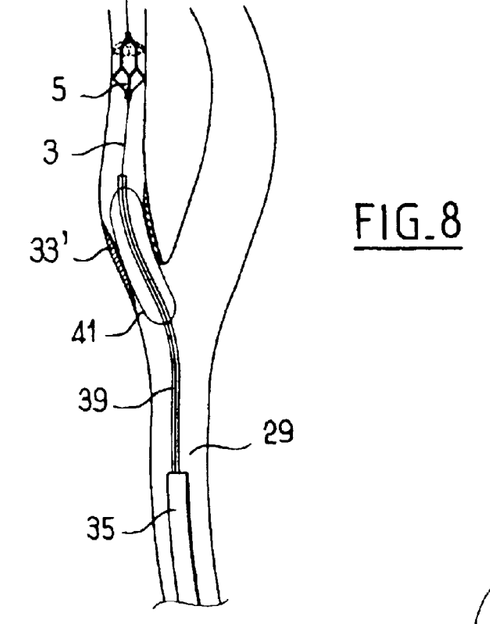

The balloon is positioned, in its deflated state, in the region of the stenosis 33. The balloon is then inflated, which causes the stenosis to dilate, as illustrated in FIG. 8.

After dilation, the balloon 41 is deflated and withdrawn with the catheter 39 (again through the catheter guide 35).

Clearly, the balloon 41 is fixed to the catheter 39 and a passage through the catheter 39 allows the inflating fluid to be fed into and back out of the balloon.

Dilation of the stenosis risks causing the detachment of vascular debris which may give rise to embolisms, even after the balloon has been withdrawn. The filtering element 5 is there to hold this debris back.

Figure 9:
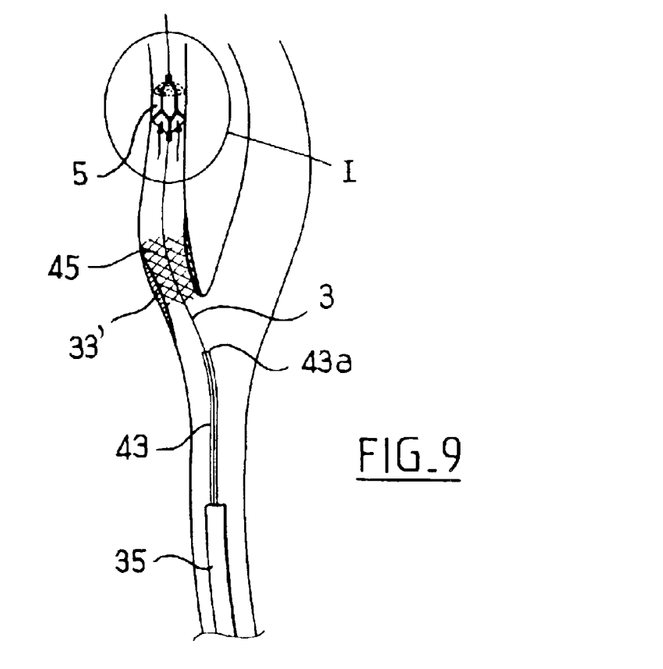

Once the catheter and balloon have been removed, the practitioner introduces a catheter 43, again through the catheter guide 35, for introducing a radially expandable implant, commonly known as a "stent".

For introduction purposes, the stent, like the filtering element illustrated in FIG. 5, is packaged inside the catheter 43 in a radially clamped state. Once the distal end 43a of the catheter 43 has been positioned on a level with the crushed stenosis 33', the catheter 43 is pulled back towards the rear, whilst a push-rod (not illustrated) enables the stent to be moved out from the catheter 43 and radially deployed (if it is self-expanding like the stent schematically illustrated as 45 in FIG. 9) or to be radially deformed by means of an internal inflatable balloon (this solution is not illustrated). By whatever means, the stent is radially deployed at the location of the stenosis 33' so that the vascular passage remains open.

The catheter 43 is withdrawn through the catheter guide 35.

Since it was put in place, the temporary filter 5 has picked up vascular debris 47 but has not prevented the blood from circulating in the inner carotid 11 (see the arrow in FIG. 9).

Together with the blood, the vascular debris 47 will penetrate and accumulate in the interior of the membrane 9, via the access openings 49 provided between the branches 70, on the proximal side 70a (see FIG. 1). The blood has been able to flow out freely via the distal orifices 15, whose section is smaller than that of the vascular debris, which is therefore trapped in the filter 5, by its membrane.

Typically, the section of the inlet orifices is equal to or greater than 0.5 mm$^2$, even in the order of from 0.2 to 0.3 cm$^2$, whereas the section of each outlet orifice 15 for the blood may be less than 0.1 mm$^2$.

Figure 10:
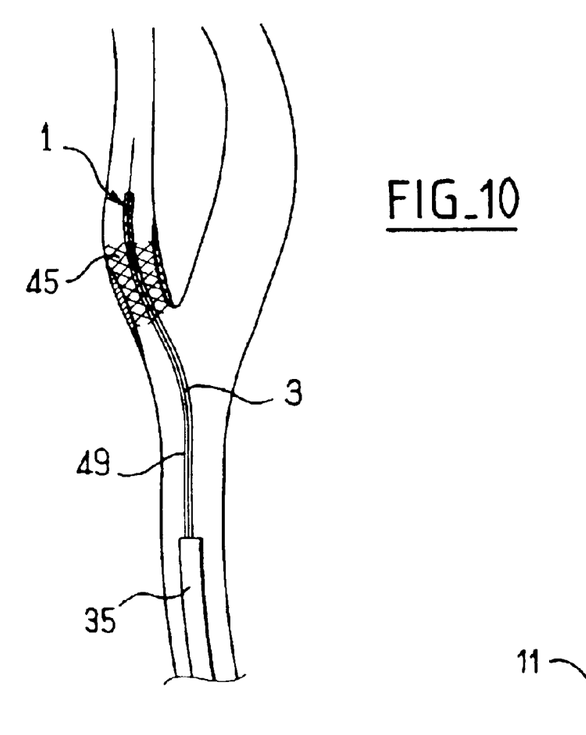
Figure 11:
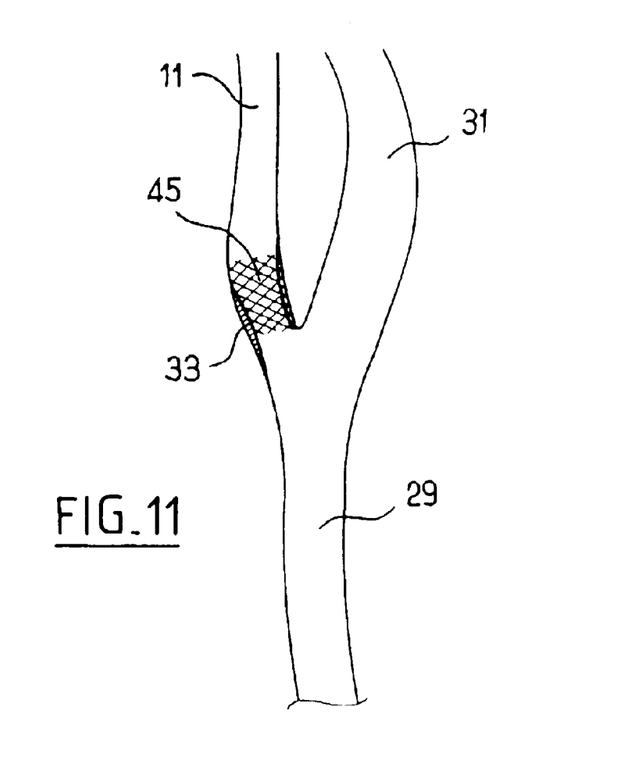

Once the practitioner deems the risk of debris migrating towards the heart to be sufficiently limited, a removal catheter 49 is introduced through the catheter-guide 35 and beyond the stent 45 and the filtering element 5 (containing the vascular debris 47) is pulled through the interior of the catheter 49 by its wire guide 3 and withdrawn, as illustrated in FIG. 10.

The catheter 49 containing the distal vascular protection system 1 is then in turn withdrawn, thus enabling the vascular debris to be extracted from the patient's body.

It should be pointed out that since the insertion catheter 37 was removed (FIG. 6), the wire guide 3 of the vascular protection system 1 has enabled the different catheters 39, 43, . . . to be guided as far as the region where they are positioned.

On completion of the intervention, the catheter guide 35 (of a larger diameter than the other catheters) is withdrawn from the patient's body and the access in the region of the skin 13 is closed.

Only the stent 45 is left in place.

Using the vascular protection system proposed by the invention for the purpose of the intervention procedure described above enables the practitioner to ensure that the blood is temporarily filtered, significantly limiting the risk of embolism.

Figure 12:
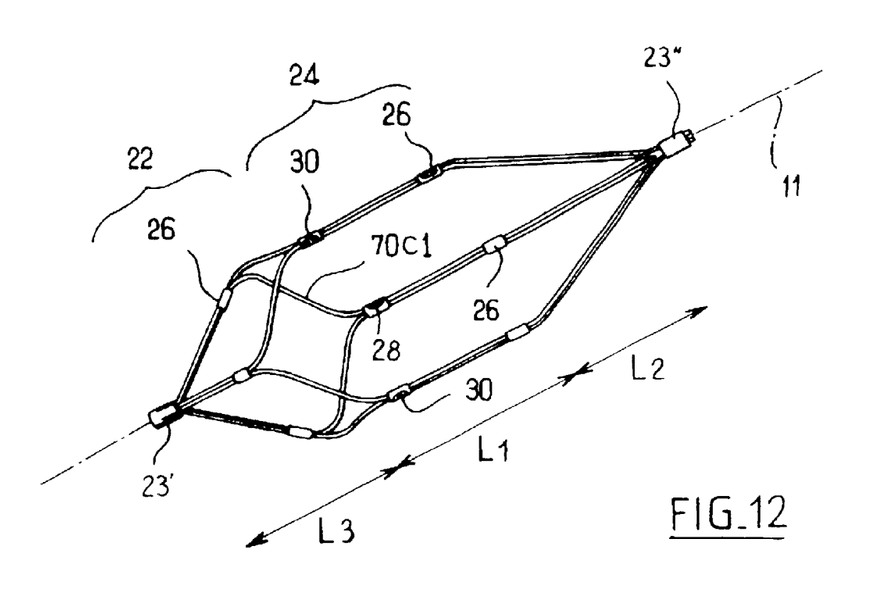
FIG. 12 shows the solution illustrated in FIG. 1 from a slightly different perspective, on a slightly smaller scale, without membrane and without control guide wire.

As may be seen from turning to FIG. 12:
the axial lengths $L_1$, $L_2$, $L_3$ are the same,
when the device 1 is in the radially expanded state, the successive conical (22) then cylindrical (24) portions of the wires are joined by "S"-shaped filament sections such as portion $70_{c1}$, these intermediate connecting portions constituting the only part where the wires are single and not grouped at least in pairs, edge to edge, and intermediate rings such as 26 are interposed at points in regions between the end rings 23' and 23".

The purpose of the rings 26 is to hold the wires together, edge to edge, along the length where they must be joined and also act as radio-opaque markers.

The rings may therefore be made of metal, in particular.

The rings enclose the wires, placed edge to edge, and it is by means of openings, such as 28, through the wall of the rings that the wires are thus joined to one another by welding (see weld spots 30). This technique limits the stress which the wires must withstand (and they are therefore not only welded in pairs but also held clamped by the rings) and produces a very favorable effect of radio opacity.

Figure 13:
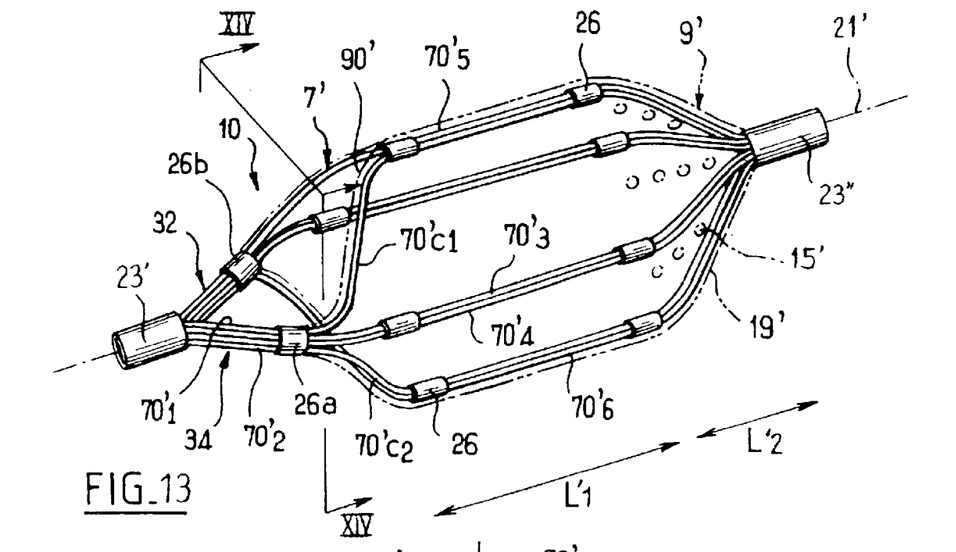
FIG. 13 is a perspective view on the same scale as FIG. 1 illustrating an improved solution of the filtering device proposed by the invention.
Figure 14:
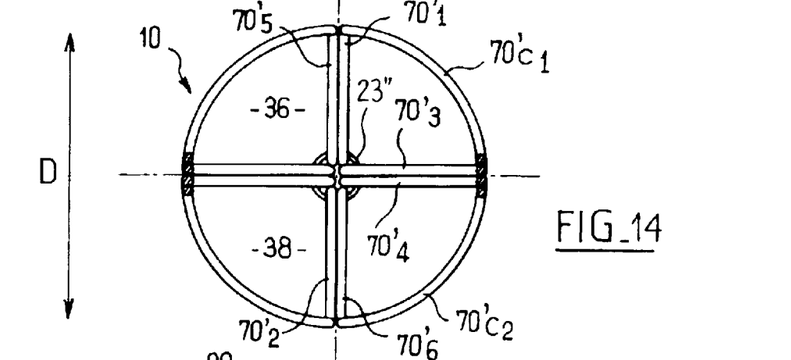
FIG. 14 is a view along section XIV—XIV indicated in FIG. 13.

FIGS. 13 and 14 illustrate another filtering element 10 proposed by the invention, which may be used as a distal protection device.

In FIG. 13, two proximal groups 32, 34 of four wires each extend from the proximal ring 23', forming part of the radially expandable structure of the filtering element 10.

The wires in each group are mutually parallel, adjacent and in this instance rectilinear. They extend along the generalities of the proximal cone defined by the structure. At the point of the maximum diameter D to which the structure is radially expandable, or close to this diameter, some wires in each group are parted from other wires in the same group and join wires of the other group a little farther along the length, where the structure is already cylindrical (length $L'_1$). In this respect, for a diameter D of the structure 10 in its radially open state, the length $L'_1$ will be such that $L'_1 > 1,5$ D, $L'_1$ being the length of the substantially cylindrical part of the structure in this state.

In the example illustrated, the angular position of the wires does not change until the distal ring 23", i.e. the wires (in this instance thus joined in pairs) will remain parallel and adjacent in pairs across the remaining length of the cylindrical portion (length $L'_1$) and then on the distal conical part (length $L'_2$). Particularly in the case of elastic wires $70'_1$ and $70'_2$, their portion ($70_{c1}$ or $70'_{c2}$) inter-connecting the proximal (group 34) and more distal grouping zones, already pointed out with respect to FIG. 1, exhibit the "S" shape.

In the region of the curved intermediate portion where the wires in question have a radial component, said wires, such as $70'_1$ and $70'_2$, are single. It is in this region that the impermeable membrane (to liquid, in particular blood) indicated by dotted-dashed lines 9' terminates, at its open proximal end 90', said membrane being closed however at its opposite distal end, in the region of its base wall 19', where the outlet openings 15' for the blood are located. As may also be seen from FIG. 13, at the point where the groups of wires part (for example in the region of the ring 26a in the case of the group of wires 34), two of the four wires part (wires $70'_1$ and $70'_2$), whereas the other two remain together in an adjacent arrangement ($70'_3$ and $70'_4$,) and remain so, in this particular instance, along the entire remainder of their length, i.e. they remain parallel and one against the other until the distal ring 23".

As with the case of the structure described above in relation to FIG. 1, wire $70'_1$ will rejoin wire $70'_5$ of the other group, as does wire $70'_2$ which will rejoin wire $70'_6$ of the second group each time, thus with an angular offset to pass from one group to the other, i.e. a radial component in the region of zones such as $701'_{c1}$ and $70'_{c2}$.

Accordingly, two large openings 36, 38 can be defined on the proximal side of the structure 10, the two openings being separated from one another by the proximal groups 32, 34 of wires, and being so until the rings 26a, 26b at which the intermediate linking portions with an "S"-shaped radial component, such as $70'_{c1}$ and $70'_{c2}$ commence.

Just as the proximal and distal rings 23', 23" clamp and axially hold the respective ends of the elastic wires (as may be seen more particularly in FIG. 14), so the intermediate, radio-opaque rings, such as 26a, 26b, retain the wires in said positions in the same way as described above with reference to the rings 26 illustrated in FIG. 12.

This FIG. 14 also clearly shows the two large openings 36, 38 as well as the shaping of the peripheral, intermediate, linking portions such as $70'_{c1}$ et $70'_{c2}$ with the radial component.

By preference, the radio-opaque rings 26 will mark the start and end of the cylinder portion of length $L'_1$.

When the structure 10 is in the radially clamped state, the elastic wires, if they are self-expanding, are deformed and constrained so that they extend substantially parallel with the axis 21' (except for the inter-connecting portions such as $70'_{c1}$ and $70'_{c2}$), the portions re-assuming their natural, radially deployed, arched shape once released.

Alternatively, it would also be conceivable to use a pull or even another expansion means to move the two rings 23', 23" mechanically in the axial direction towards or apart from one another.

It should be pointed out that instead of proximal groups such as 34 with four wires, it would also be possible to provide at least two groups of three wires each, the wires of each group parting from one another sooner, in which case two of the wires in each of these groups will then rejoin a wire of the other group, whilst the third wire will remain single for the remainder of the length of the structure until the distal ring 23".

On the basis of this hypothesis, there would then be two groups of two diametrically opposed wires on the cylindrical portion of the length $L'_1$ as well as two groups of a single wire also diametrically opposed, whereas FIG. 13 shows four groups each of two wires, both along the length $L'_1$ and along the length $L'_2$.

This angular distribution may also be seen in FIG. 14.

Figure 15:
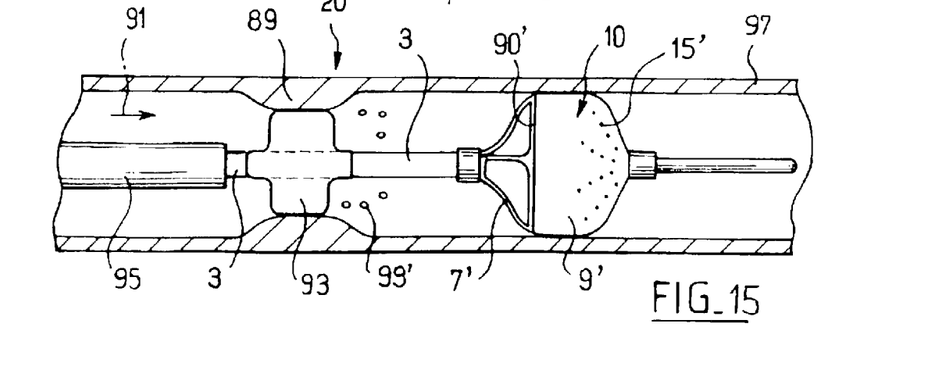
FIG. 15 is a schematic diagram in longitudinal section of apparatus such as used for angioplasty treatment, fitted with the filtering device with distal protection proposed by the invention.

In FIG. 15, the filtration device 10 belongs to an angioplasty apparatus 20. More generally, at the end of its wire guide 3 (which in this instance is a catheter), the device 10 may be used in particular as a distal protection device for equipment used for vascular treatment anywhere where there is a risk of a the blood flow carrying embolic materials, where migration to the heart or brain might prove dangerous.

The filtering structure 10 is disposed downstream of the stenosis 89 constituting the intervention region in FIG. 15 (the direction of blood flow being indicated by arrow 91). It will therefore enable this blood to be filtered by holding back the embolic particles (orifices 15'being of a section smaller than the size of the materials), without inasmuch substantially interrupting the blood circulation. It should also be pointed out that the feature whereby $L_1$(or $L'_1$)>1,5 D improves the sealing properties, centering and efficiency of the filtering structure.

The apparatus 20 has a balloon 93, which may be radially inflated via the catheter 3 to which it is fixed.

Both the balloon 93 and the filtering device 10 are designed to be radially contained, during their vascular implantation, in an insertion/removal sheath 95 designed to pass through the patient's body as far as the vascular region concerned.

The respective lengths of the sheath 95 and the maneuvering means (catheter 3) are at least equal to the distance separating the vascular intervention zone (zone of the stenosis) from the cutaneous surface of the patient's body, from which the intervention device is implanted by endoluminal access.

If it is self-expanding, the filtering device 10 expands radially on emerging from the sheath 95. In any event, the structure of the device 10 can be radially expanded by mechanical means.

The balloon 93, which may be an angioplasty balloon, is inflated with a fluid circulating either through the catheter 3, or through a separate tube (not illustrated) to which it would then be attached.

In FIG. 15, the radial expansion of the balloon 93 has widened the vessel 97 at the point of the stenosis 89 facing which the balloon was disposed.

Beforehand (or simultaneously), the filtering structure 10 had been radially deployed to close off the vessel downstream of the location of the stenosis and the balloon.

Applying the balloon against the vessel wall typically causes embolic materials such as 99 to detach, which have a tendency to migrate downstream, entrained with the flow.

They are prevented from migrating by the filtering device 10.

Finally and as illustrated, it is to be noted that the border line defined by the portions of wires (70, $70'_1$, $70'_2$, . . . ,) surrounding the inlet openings 36, 38, delimited a series of deformable polyeders (angularly located around the axis 11 of the blood filtering element).

Precisely, these polyeders (each having substantially the shape of a quadrilater) extend between the proximal line 90 of the membrane and the proximal end of the wires (ring 23). So, the proximal end 90 of the membrane partially define said deformable adjacent polyeders which extend obliquely with respect to the axis 11, when the blood filtering device is in its radially expanded state. All together, the polyeders define the above-mentioned proximal cone of the blood filtering structure. So, the diameter of the blood filtering element is self-adaptable to the diameter of the duct (blood vessel) in which it is implanted.

What is claimed is:

1. A vascular protection system adapted to be implanted through an endoluminal access in a blood vessel having a vessel wall, the protection system comprising a blood filtering element which is permeable to blood but impermeable to embolic materials, the blood filtering element having an axis, proximal and distal ends along the axis and inlet openings for entering blood and embolic materials into the blood filtering elements, said blood filtering elements being radially expandable or radially shrinkable with respect to the axis and comprising a supporting structure connected to a membrane having a proximal edge, the supporting structure peripherally comprising a series of wires having a length between the proximal and distal ends, said supporting structure locally defining a substantially continuous peripheral mouth maintaining the proximal edge of the membrane for engaging the vessel wall, and the supporting structure comprising, from the proximal end to the distal end, firstly at least two groups of wires, each comprising at least two adjacent wires, the groups splitting up at a location along the length of the wires, so that among said groups, at least two wires of a group diverge from each other, then, farther on said length but before the distal end, a wire of a determined group which have diverged from at least one other wire of the same group joins a wire of another group.

2. The system according to claim 1, wherein:
each wire has a proximal portion and a distal portion, and
in the immediate vicinity of the proximal edge of the membrane, an intermediate portion is interposed and connected between the proximal portion and the distal portion of the wires, the intermediate portion extending transversal to the axis and the intermediate portions of two of said wires angularly adjacent around said axis having ends located close to each other.

3. The system according to claim 1, wherein:
the wires have a proximal end and a distal end where said wires are connected together by a proximal ring and a distal ring, respectively, and
the proximal and distal portions of several of said angularly adjacent wires are substantially parallel and adjacent to each other, and have an angular shifting of one wire, round the axis, between the adjacent locations of said wires along their proximal portion and their distal portion.

4. The system according to claim 2, wherein the filtering element has a radially expanded state in which the proximal portions of the wires define together a proximal cone and the distal portions of said wires define together substantially a cylinder connected to a distal cone where the filtering member is permeable to blood, the cylinder of the distal portions being connected to the proximal cone substantially at the proximal edge of the membrane, by the intermediate portions of the wires.

5. The system according to claim 4, wherein the filtering membrane is blood tight along the cylinder, and has holes therethrough at the location of the distal cone, for allowing the blood to flow there, while holding embolic materials.

6. The system according to claim 2, wherein the intermediate portion of one of said wires is connected by rounded bends to both the proximal portion and the distal portion, the rounded bends having an angle comprised between 90° and 135° with respect to the axis.

7. The system according to claim 1, wherein the filtering membrane covers and is supported by the supporting structure between its proximal edge up to the distal end of the filtering element, the supporting structure locally having, together with the filtering membrane, a cylindrical shape in the radially expanded state of the filtering element, so that a cylindrical blood tight surface is defined thereby with respect to a vascular wall of the blood vessel where the protecting system is to be implanted.

8. The system according to claim 4, wherein the cylindrical blood tight surface has an axial length longer than the axial length of the proximal and distal cones.

9. A vascular protection system, adapted to be implanted through an endoluminal access in a blood vessel having a vessel wall, the protection system comprising a blood filtering element which is permeable to blood but impermeable to embolic materials, the blood filtering element having an axis, proximal and distal ends along the axis and inlet openings for entering blood and embolic materials into the blood filtering elements, said blood filtering elements being radially expandable or radially shrinkable with respect to the axis and comprising a supporting structure connected to a membrane having a proximal edge, the supporting structure peripherally comprising a series of wires having a length between the proximal and distal ends, said supporting structure locally defining a substantially continuous peripheral mouth maintaining the proximal edge of the membrane for engaging the vessel wall; and
wherein the supporting structure comprises from the proximal end to the distal end, firstly at least two groups of wires, each comprising more than two adjacent wires, the groups splitting up at a location along the length of the wires, so that among said groups, at least some of the wires diverge from each other, then, farther on said length, some wires of a determined group which have diverged from at least some of other wires of the same group, being located close to at least one wire of another group of wires.

10. The system according to claim 9, wherein at the location where the groups of wires split out, at least some of the wires of a determined group diverge from other wires of the same group, whereas other wires of said determined group remain adjacent to each other on at least a portion of their length.

11. The system according to claim 1, wherein in the vicinity of the proximal end, the supporting structure exclusively comprises two groups of wires including at least four wires each, said wires splitting out locally along the length of the wires, so that, in each group, a first wire diverges on one side from the other wires of the same group, a second wire diverges on the other side, the third and fourth wires of said same group remaining adjacent, whereas, farther along said length, said first wire being located close to the first wire of another group of wires and said second wire being located close to a second wire of said other group of wires.

* * * * *